(12) United States Patent
Dayton

(10) Patent No.: US 9,814,794 B2
(45) Date of Patent: Nov. 14, 2017

(54) DECONTAMINATION ENCLOSURE AND METHOD

(71) Applicant: Daylight Medical, Inc., Middleburg Heights, OH (US)

(72) Inventor: Roderick Dayton, Strongsville, OH (US)

(73) Assignee: DIVERSEY, INC., Charlotte, NC (US)

( * ) Notice: Subject to any disclaimer, the term of this patent is extended or adjusted under 35 U.S.C. 154(b) by 0 days.

(21) Appl. No.: 15/350,175

(22) Filed: Nov. 14, 2016

(65) Prior Publication Data
US 2017/0056540 A1 Mar. 2, 2017

Related U.S. Application Data

(63) Continuation of application No. 15/209,257, filed on Jul. 13, 2016, now Pat. No. 9,492,577, which is a continuation of application No. PCT/US2015/058807, filed on Nov. 3, 2015.

(60) Provisional application No. 62/074,191, filed on Nov. 3, 2014.

(51) Int. Cl.
| | |
|---|---|
| *A61N 5/00* | (2006.01) |
| *G01N 21/00* | (2006.01) |
| *A61L 2/10* | (2006.01) |
| *A61L 2/24* | (2006.01) |

(52) U.S. Cl.
CPC ............. *A61L 2/10* (2013.01); *A61L 2/24* (2013.01); *A61L 2202/122* (2013.01); *A61L 2202/14* (2013.01); *A61L 2202/25* (2013.01)

(58) Field of Classification Search
CPC .............. A61L 2/00; A61L 9/18; A61L 9/20
USPC ............ 422/24, 105, 119; 250/453.11, 492.1
See application file for complete search history.

(56) References Cited

U.S. PATENT DOCUMENTS

| | | | | |
|---|---|---|---|---|
| 2004/0231696 | A1* | 11/2004 | Wen | A23L 3/28 134/1 |
| 2014/0158910 | A1* | 6/2014 | Fletcher | A61L 2/10 250/455.11 |

FOREIGN PATENT DOCUMENTS

| | | |
|---|---|---|
| KR | 20090100329 A | 9/2009 |
| KR | 20120052521 A | 5/2012 |
| RU | 65761 U1 | 8/2007 |

OTHER PUBLICATIONS

International Search Report and Written Opinion dated Feb. 11, 2016 for PCT/US2015/058807.

* cited by examiner

*Primary Examiner* — Monzer R Chorbaji
(74) *Attorney, Agent, or Firm* — Cooper Legal Group, LLC

(57) ABSTRACT

Provided are a method and apparatus for decontaminating personal protective equipment while it is being worn by a person. A booth having a plurality of internally-reflective surfaces defines an interior space with dimensions suitable for receiving a standing person wearing the personal protective equipment. A plurality of UVC light sources are arranged to emit UVC light into the booth, and are operational while the person wearing the personal protective equipment is within the interior space. A door is selectively closeable to enclose the interior space and interfere with UVC light escaping the interior of the booth into an ambient environment of the booth, and a controller is operable to selectively operate the UVC light sources while the person wearing the personal protective equipment is standing within the interior space.

20 Claims, 6 Drawing Sheets

DECONTAMINATION ENCLOSURE AND METHOD

BACKGROUND OF THE INVENTION

1. Field of the Invention

This application relates generally to a method and apparatus for decontaminating objects and, more specifically, to a method and enclosure in which clinicians wearing personal protective equipment are exposed to a decontamination agent to render the exposed surfaces of the personal protective equipment pathogen reduced.

2. Description of Related Art

Physicians, nurses, aid workers and other clinicians who treat patients with infectious diseases often wear personal protection equipment ("PPE") to limit their exposure to the pathogen. During treatment, exposed surfaces of the PPE will often come into contact with the bodily fluids of patients, and become contaminated with the pathogen. Pathogens on the PPE can be carried to transitional areas where the clinicians remove their PPE, and remain viable to infect the clinicians and others within the vicinity for extended periods of time, thereby defeating the purpose of wearing the PPE in the first place.

Traditional decontamination efforts have included dousing the PPE in bleach or other disinfectant before the PPE is removed from the clinicians. Although effective, liquid disinfectants such as bleach commonly contain active ingredients such as sodium hypochlorite, which causes irritation of the clinicians' airways and can cause skin burns. Further, in remote regions of the world liquid disinfectants may not be readily available for use, despite their potential side effects.

BRIEF SUMMARY OF THE INVENTION

Accordingly, there is a need in the art for an apparatus and method for rendering PPE pathogen reduced without first requiring removal of the PPE. Such an apparatus and method should limit the spread of a pathogen carried by the PPE to the clinician or another person without exposing the clinician wearing the PPE to harm from a decontamination agent.

According to an embodiment, the present disclosure includes a method of decontaminating personal protective equipment. Such a method includes, while a person wearing the personal protective equipment to be decontaminated is present within a booth having an internally-reflective surface, operating a plurality of UVC light sources arranged to emit UVC light into the booth. Operation of the UVC light sources is maintained while the person wearing the personal protective equipment is in the booth to expose surfaces of the personal protection equipment to the UVC light for a predetermined period of time suitable to achieve a desired level of decontamination of the surfaces of the personal protective equipment. The UVC light sources are de-energized after expiration of the predetermined period of time.

According to another embodiment, the present disclosure includes a decontamination apparatus including a booth having a plurality of internally-reflective surfaces that define an interior space having dimensions suitable for receiving a standing person wearing personal protective equipment. A plurality of UVC light sources are arranged to emit UVC light into the booth, and a door is selectively closeable to enclose the interior space and interfere with UVC light escaping the interior of the booth into an ambient environment of the booth. A controller is operable to selectively operate the UVC light sources while the person wearing the personal protective equipment is standing within the interior space.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

BRIEF DESCRIPTION OF SEVERAL VIEWS OF THE DRAWING

The invention may take physical form in certain parts and arrangement of parts, embodiments of which will be described in detail in this specification and illustrated in the accompanying drawings which form a part hereof and wherein.

DETAILED DESCRIPTION OF THE INVENTION

Figure 1:
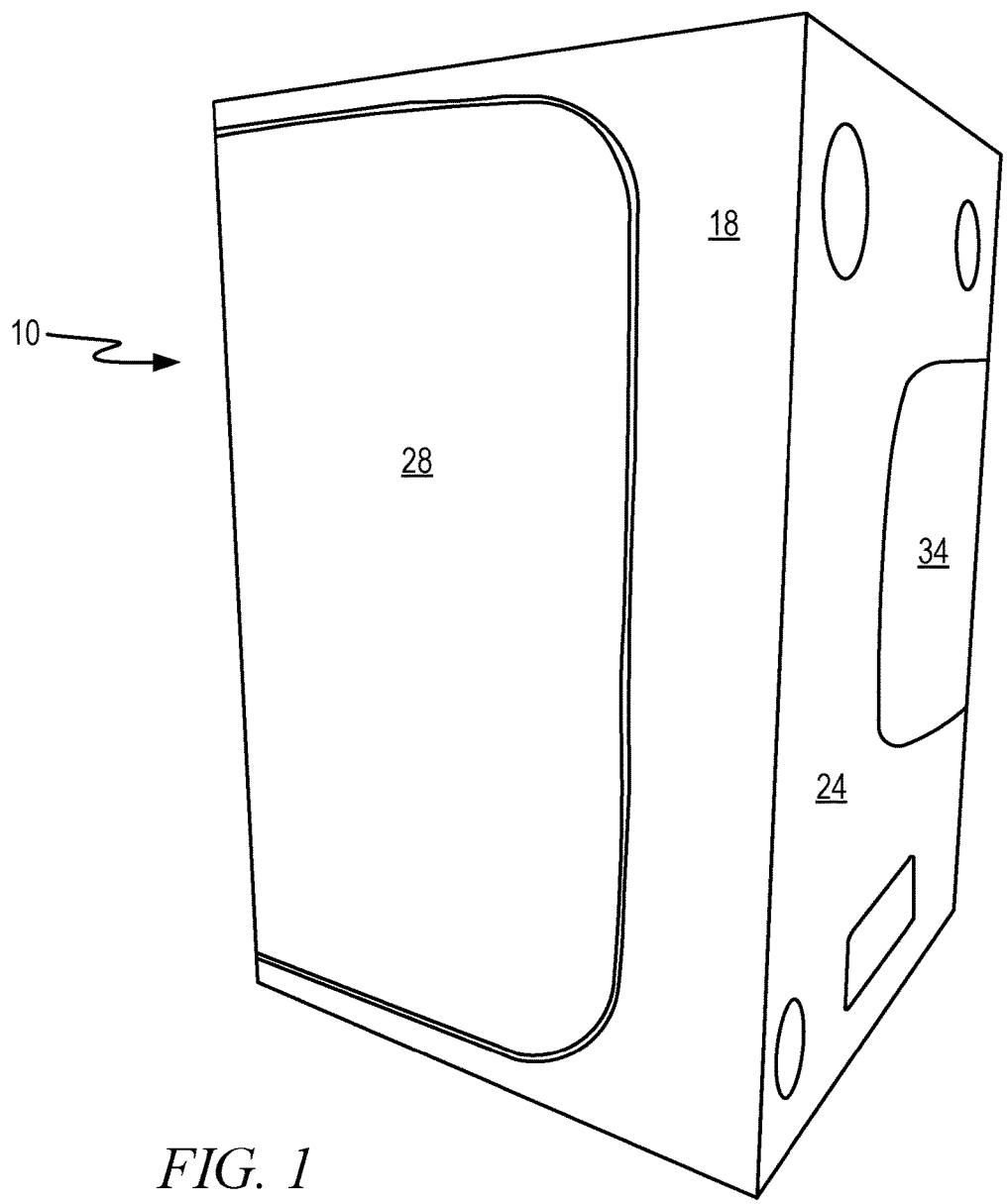
FIG. 1 is a perspective view of a decontamination booth in a closed state in which PPE worn by a clinician is to be rendered pathogen reduced.

Certain terminology is used herein for convenience only and is not to be taken as a limitation on the present invention. Relative language used herein is best understood with reference to the drawings, in which like numerals are used to identify like or similar items. Further, in the drawings, certain features may be shown in somewhat schematic form.

It is also to be noted that the phrase "at least one of", if used herein, followed by a plurality of members herein means one of the members, or a combination of more than one of the members. For example, the phrase "at least one of a first widget and a second widget" means in the present application: the first widget, the second widget, or the first widget and the second widget. Likewise, "at least one of a first widget, a second widget and a third widget" means in the present application: the first widget, the second widget, the third widget, the first widget and the second widget, the first widget and the third widget, the second widget and the third widget, or the first widget and the second widget and the third widget.

FIG. 1 shows an illustrative embodiment of a decontamination booth 10 in which personal protection equipment ("PPE") 12 (FIG. 3) being worn by a clinician 14 can be decontaminated, thereby rendering the PPE 12 pathogen reduced. Rendering the PPE 12 "pathogen reduced" does not necessarily require the surfaces of the PPE to be 100% sterile, free of any and all living organisms that can viably reproduce. Instead, to be considered pathogen reduced, there must be a lower level of living contagions on the decontaminated PPE 12 capable of reproducing or otherwise causing an infection after performance of the decontamination process than the level that existed on the PPE 12 prior to performance of the decontamination process. For example, the exterior surfaces of the PPE 12 can be considered to be pathogen reduced if at least a 1 $\log_{10}$ reduction of such contagions on the exposed surfaces remain infectious (i.e., no more than 1/10th of the biologically-active contagions originally on the exposed surfaces of the PPE 12 remain active or infectious at a time when the decontamination process is completed). According to yet other embodiments, the surfaces of the PPE 12 can be considered pathogen reduced once at least a 3 $\log_{10}$ reduction (i.e., 1/1,000th) of such contagions on the exterior surfaces of the PPE 12 is achieved.

Figure 3:
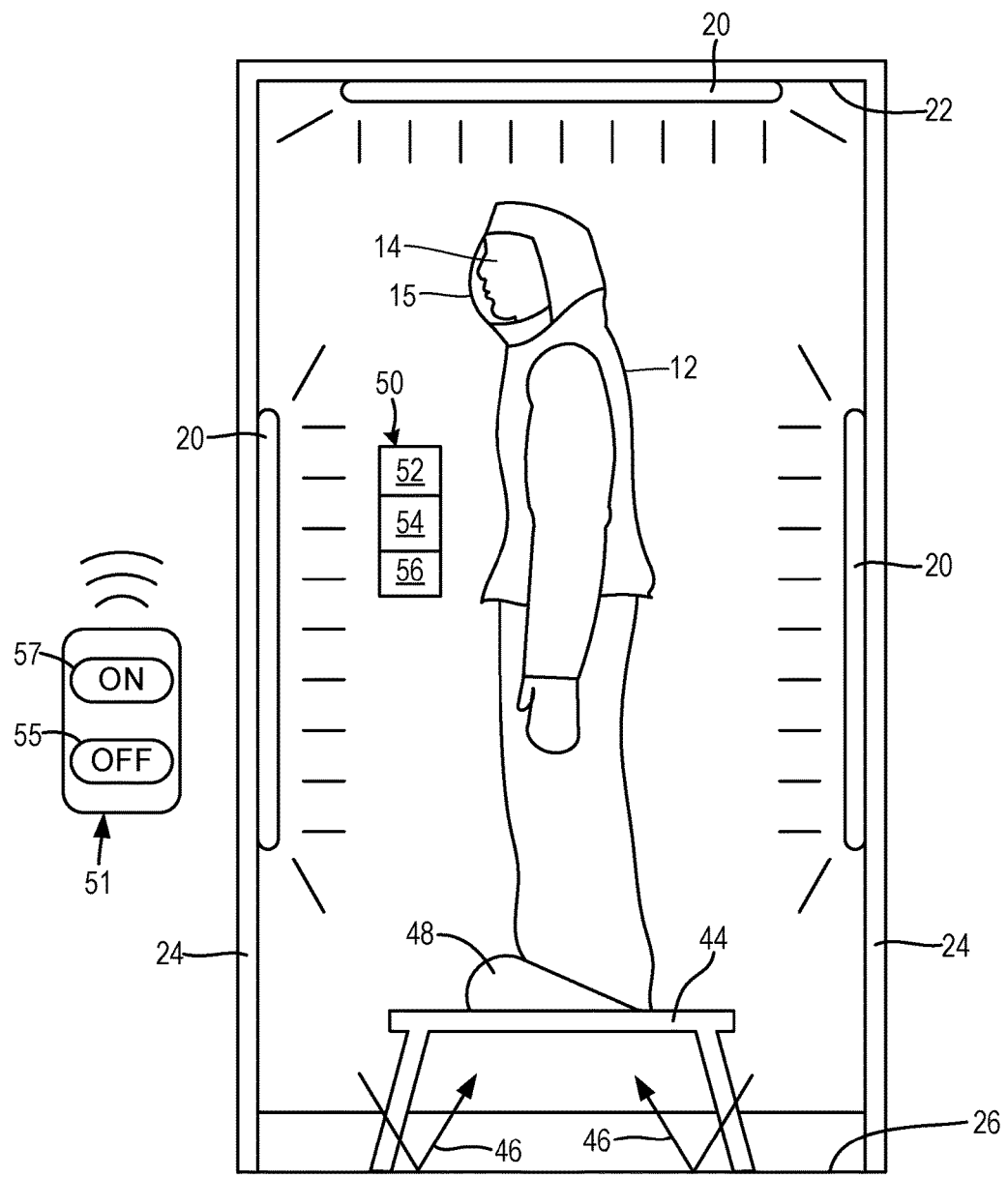
FIG. 3 is a partially cutaway view of a decontamination booth in which a clinician wearing PPE is being exposed to UVC light as a decontamination agent, wherein the clinician is standing on a platform 44 (FIG. 3) that is substantially transparent to UVC light to expose the bottom of the clinician's footwear to the UVC light through the platform.

According to the embodiment shown in FIG. 3, the PPE 12 can include any protective garments and/or equipment worn to protect clinicians from pathogens, such as pants, jackets, gloves, overalls, coveralls, hazmat suits, goggles, masks, face shields, helmets, hats, shoes, shoe covers, self-contained breathing apparatuses, etc. Such articles of PPE 12 can optionally be airtight, and can optionally be substantially opaque to certain wavelengths of light. For example, the articles of PPE 12 can be substantially opaque to ultraviolet C ("UVC") light, which is electromagnetic radiation with a wavelength from approximately 280 nm to approximately 100 nm. To be substantially opaque to this light, the articles 12 can block at least 90% of UVC light, and optionally at least 95% of UVC light imparted thereon.

Figure 2:
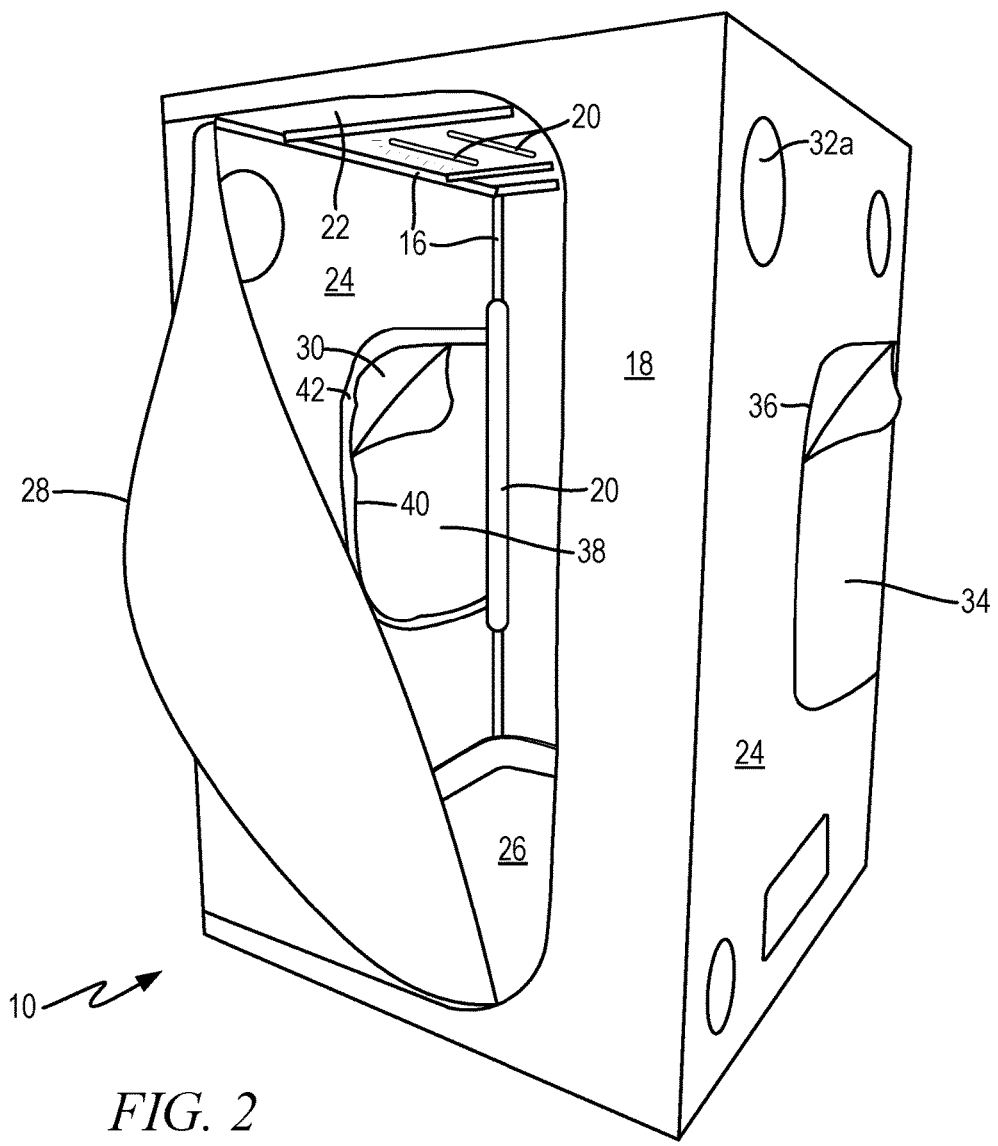
FIG. 2 is a perspective view of the decontamination booth shown in FIG. 1 in an open state, allowing the entry and exit of a clinician wearing PPE.

The decontamination booth 10, as shown in FIGS. 1 and 2, includes a rigid frame 16 that supports a shell 18 made from a flexible material to form a cubical enclosure in which the PPE 12 worn by the clinician 14 is to be exposed to a decontamination agent and rendered pathogen reduced. The frame 16 can be formed from a plurality of interlocking segments. For example, each segment can include both a male end and a female end. The segments can be assembled end to end by inserting the male end of one segment into the female end of another segment, optionally by hand and without the assistance of any tools. The segments can optionally be urged together, when assembled, by an elastic band that extends through an interior passage defined by each segment. But regardless of their configuration, the segments can be repeatedly disassembled without damaging the segments to allow for transportation of the decontamination booth 10 and assembled to support the shell 18 that will define the cubical, or other shaped of enclosure that can be closed to interfere with the escape of UVC light or other decontamination agent.

When relocation of the decontamination booth 10 is desired, the segments can be pulled apart and arranged parallel to each other or otherwise broken down into a size that fits into a bag or other portable container to be carried by hand. The decontamination booth can optionally be used in conjunction with a hand-held, battery operated UVC source (not shown) that can be used to emit limited quantities of UVC light for testing the UVC protection offered by the PPE 12 worn by the clinician 14. For example, the hand-held, battery operated UVC source can be activated adjacent to a portion of the PPE 12 pulled away from the clinician 14 wearing it. A hand-held UVC meter can also be positioned adjacent to the portion of the PPE 12, but separated from the hand-held, battery operated UVC source by the portion of the PPE 12 to give the clinician 14 a sense of the UVC blocking ability offered by the PPE 12 prior to the performance of a decontamination process within the decontamination booth 10 while wearing the PPE 12.

For the sake of brevity and clarity, the decontamination agent will be described herein below as UVC light. One or a plurality of UVC light sources 20 (e.g., UVC bulbs) that emit UVC light to be directed toward the surface(s) to be rendered pathogen reduced can be supported within the decontamination booth 10. As shown in FIGS. 1 and 3, a UVC light source 20 is supported by the frame 16 adjacent to each corner of the decontamination booth 10, and adjacent to the ceiling 22 of the decontamination booth 10. The UVC light source(s) 20 described herein can be operatively connected to a power plug that is to be inserted into a conventional AC mains electrical socket supplied with electricity by a public utility, for example. According to alternate embodiments, electric energy can be supplied by a rechargeable battery bank 25 (FIG. 5) operatively connected to the UVC light source(s) 20. Regardless of the power supply, embodiments of the decontamination booth 10 can include at least two, and optionally three or four UVC bulbs that can each optionally be independently controlled relative to the others. For example, each UVC source 20 can exhibit a minimum fluence of approximately 1 $mW/s/cm^2$, or 145 mJ per five minute cycle measured at twenty five (25 in.) inches from the respective source 20.

Figure 6:
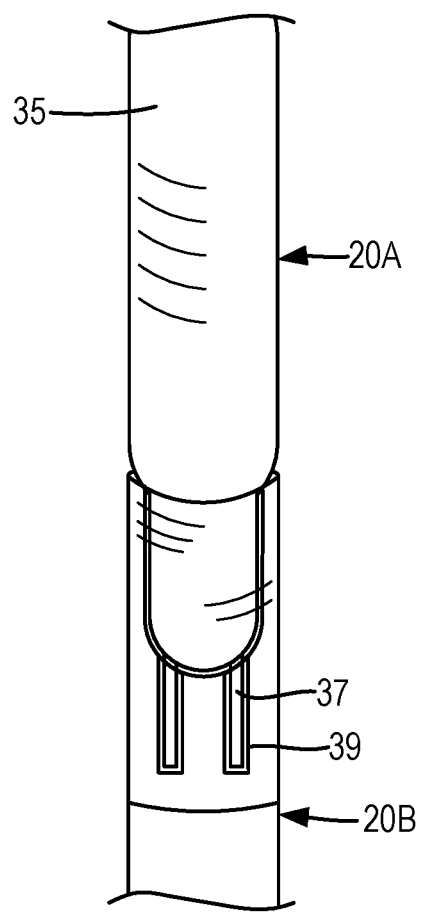
FIG. 6 is a perspective view of two UVC bulbs connected in series.

Embodiments of the UVC light sources 20 include UVC bulbs 20A and 20B that can be connected in series in an end-to-end arrangement as illustrated in FIG. 6. Each bulb 20A, 20B can optionally share a common configuration with the other bulb 20A, 20B. So configured, the bulbs 20A, 20B includes a cylindrical glass tube region 35 with a male electrical connector 37 provided to a first end and a female electrical socket 39 arranged at an opposite end along a longitudinal axis of the bulbs 20A, 20B. The male electrical connector 37 provided to the end of the bulb 20B not shown in FIG. 6 can be plugged into base with a compatible female electrical socket 39. The base can optionally include a controller 50 described below, or at least a switch that allows an operator to turn the bulb 20B on and off. The male electrical connector 37 of the other bulb 20A, which can include a metallic contact or other plug feature as shown in FIG. 6, can be inserted into the female electrical socket 39, which can include a sleeve lined with a metal substance or other electrical conductor, of the other bulb 20A to establish an electrical connection between the bulbs 20B, 20A. Electric energy conducted between the female electrical socket 39 and the male electrical connector 35 energizes the bulb 20A. The bulb 20B plugged directly into the base is controlled by the controller 50 or other suitable control device and is considered to be the "master" bulb, while the bulb 20A and any other bulb electrically connected to the master bulb 20B are considered "slave" bulbs, as their operation is dependent upon, and limited to the operational state of the master bulb 20B in the present example.

The shell 18 can be formed from any suitably-flexible material such as a woven fabric, cross-woven ballistic Nylon, and the like, or a combination including a plurality of different types of flexible material. At least a portion of the material forming the shell 18 can optionally be foldable, allowing the shell 18 to be broken down and optionally folded into a size that allows for transportation of the shell 18, by hand, in a bag or other suitable container. When deployed, the shell 18 includes at least side walls 24, a ceiling 22, a floor 26, and a door flap 28. The interior dimensions of the decontamination booth 10 can be any desired value, allowing an adult human, for example, to stand therein without hitting their head on the ceiling. For such embodiments, the floor 26 of the decontamination booth 10 can measure approximately 4.5 ft. by 4.5 ft. (e.g., approximately 20 sq. ft.), and the side walls 24 can be at least approximately 7 ft. in height, however, the dimensions can vary to accommodate any object that is to be decontaminated within the decontamination booth 10. For example, the interior of the decontamination booth can have a height of at least 6 ft. Alternate embodiments of the shell 18 can include at least one of: a window 30, and one or more vents 32. If present, the window 30 can optionally be formed of an optically transparent sheet of plastic, glass or other suitable material to allow an occupant of the decontamination booth 10 to view the environment outside of the decontamination booth 18. Although optically transparent, the plastic, glass or other material forming the window 30 can block, or at least interfere with the transmission of UVC light, even while not concealed as described below. For instance, the material can block at least 90% of the UVC light, or at least 95% according to alternate embodiments. The one or more windows 30 can also optionally be concealed from outside of the shell 18 by a window flap 34 that, when closed, further interferes with the emission of UVC light from the source(s) 20 within the shell 18. The window flap 34 can be formed of the same flexible material that is opaque to UVC light forming the other portions of the shell 18 (e.g., the walls 24, ceiling 22 and floor 26), and can be secured in place over the window 30 through the use of any releasable fastener. For instance, the releasable fastener can include a zipper assembly that extends about a significant portion (e.g., ¾) of the periphery 36 of the window 30. An additional window flap 38 can also optionally be arranged to cover the interior of the window 30, to be opened and closed by the occupant of the decontamination booth 10 utilizing any suitable releasable fastener (e.g., zipper assembly about the periphery 40) that allows the additional window flap 38 to be repeatedly opened and closed to selectively grant access to the window 30 from the inside.

If present, the one or more vents 32 can form an aperture in a vertical wall 24 of the shell 18 to allow air to enter and/or exit the interior of the decontamination booth 10. The vent(s) 32 can include a thermal vent 32a (FIG. 2), through which air travels as a result of a temperature gradient between the interior of the decontamination booth 10 and the ambient, external environment of the decontamination booth 10. According to alternate embodiments, the vent(s) 32 can optionally include one or more forced-air vents 32b (FIG. 5), each including an aperture formed in a vertical wall 24 of the shell 18 in fluid communication with a fan, blower or any suitable air mover 17 (FIG. 5) that is operable to move air into the interior of the decontamination booth 10 through the forced-air vent 32. For example, the air mover 17 can move any suitable volume of air (e.g., 180 cfm) at a rate that can be exhausted through the one or more thermal vents 32a, for example, so as to protect against undesirable inflation of the decontamination booth 10. Each vent 32 can optionally and independently include a segment of material to interfere with the direct transfer of objects through the walls 24, but such segments of material may optionally not hermetically seal the aperture of the respective vent(s) 32.

The door flap 28 can also be formed from a segment of the same material from which the walls 24, ceiling 22 and floor 26 are formed. And like the window flaps 34, 38, the door flap 28 can be closed through the use of a releasable fastener such as a zipper assembly that extends at least partially (e.g., about ½ to about ¾ of the circumference) of the door flap 28 to allow for ready ingress to and egress from the decontamination booth 10. The door flap 28 can optionally be configured to be manipulated from inside the decontamination booth 10 and from outside the decontamination booth 10. For example, a zipper mechanism can include a handle segment that can be grasped from inside and/or outside of the decontamination booth 10.

To further interfere with the escape of UVC light from within the decontamination chamber 10, at least one, and optionally each releasable fastener utilized to secure the window flap(s) 34, 38 and the door flap 28 closed can optionally include a light shield 42. An example of such a light shield 42 can include a strip of material that is opaque to UVC light, and extends over at least a portion of the zipper when the cooperating portions of the zipper are mated to maintain the window flap(s) 34, 38 and/or the door flap 28 closed. According to alternate embodiments, the zippers can include tightly-meshing teeth that, when mated, block substantially all of the UVC light emitted within the decontamination booth 10. Thus, the decontamination booth 10 can block at least 95%, and optionally at least 99% of all UVC light emitted therein, preventing the blocked light from reaching the ambient environment of the decontamination booth 10.

The inward-facing surface (e.g., the surface viewable from within the decontamination chamber 10 with all flaps closed) of at least one, optionally a plurality of or all portions (e.g., floor, walls, ceiling, flap(s), etc.) of the shell 18 can be provided with a reflective material that reflects UVC light. For example, the inward-facing surface(s) can be provided with an aluminized or otherwise metalized material, Mylar (e.g., stretched polyester film, also commonly referred to as biaxially-oriented polyethylene terephthalate or "BoPET", for short) film, or any other suitable reflector of UVC light.

As shown in FIG. 3, the decontamination booth 10 can optionally include a platform 44, false floor or other support on which the clinician 14 wearing the PPE 12 can stand to be supported at an elevation vertically above the floor 26 during a decontamination process. At least a portion of the platform 44 on which the clinician 14 stands can be formed from a material that is substantially transparent (e.g., degrades intensity of UVC light no more than 50%, or no more than 30% according to an alternate embodiment, or no more than 20% according to yet another embodiment) to UVC light. Thus, at least a portion of UVC light 46 emitted by the source(s) 20 and reflected upwardly by the reflective surface of the floor 26 can pass through the platform 44 to be imparted on the underside of the clinician's footwear 48.

A controller 50 can also optionally be supported within the decontamination booth 10 to allow the clinician 14 to initiate a decontamination process and, optionally, manually terminate a decontamination process already underway. The controller 50 can include at least one of a start button 52 that can be pressed by the clinician 14 while inside the decontamination booth 10 to initiate a decontamination process during which the sources 20 are energized, a stop button 54 that can be pressed by the clinician 14 while inside the decontamination booth 10 to terminate a decontamination process to de-energize the sources 20; and a timer 56 that is operable to time a decontamination process and automatically (e.g., without human intervention) initiate termination of the decontamination process in response to expiration of a predetermined period of time to achieve the desired level of decontamination. For example, the timer 56 can be set for any desired length of time that, once expired, causes the sources 20 to be automatically de-energized. By default, the duration of the decontamination process as determined by the timer 56 can be established at five (5 min.) minutes, but other values can optionally also be utilized. Using the default value, once a decontamination process is initiated, the sources 20 will be automatically de-energized in response to expiration of the timer 56. According to alternate embodiments, the duration of the decontamination process to be established by the timer 56 can be adjusted, and/or a plurality of pre-programmed durations can be included as default values of the timer 56. For example, the timer 56 can optionally be provided with a plurality of buttons, each assigned a different, dedicated duration. Selecting such a button initiates the decontamination process and causes the sources 20 to be energized for the duration corresponding to the selected button. The timer 56 can optionally be capable of being programmed, in real time by a user and/or pre-programmed by a manufacturer, to conduct decontamination cycles as short as one minute, and as long as twenty four (24 hr.) hours.

The controller 50 can optionally also be provided with a sensing component that can receive a signal or otherwise sense a breach of the decontamination booth 10 while a decontamination process is underway. For example, the controller 50 can be provided with a light sensor that can detect certain changes in light (e.g., changes in the level of visible light outside of the UVC range) within the decontamination chamber 10. The controller 50, based on such sensed light gradients, can determine that the door flap 28 has been opened and terminate the decontamination process to de-energize the sources 20. Of course, a light sensor is but one of several suitable sensors that can be utilized by the controller 50 to determine that the sources 20 are to be de-energized. According to an alternate embodiment, the controller can include a motion sensor trained on the door flap 28. If the door flap 28 is opened such a motion sensor will sense this condition and transmit a signal to cause the controller 50 to de-energize the source(s) 20. According to another illustrative embodiment, a sensor in communication with the zipper provided to the periphery of the door flap 28 can sense when the zipper is opened, and again transmit a signal to cause the controller 50 to de-energize the source(s) 20. According to another embodiment, the controller 50 can be in communication with (e.g., via a wireless communication channel and/or hardwired to) a remotely-located (e.g., located and accessible by an operator outside of the decontamination booth 10) fob 51 (FIG. 3) or other remote control to receive a manually-entered termination instruction that causes the controller 50 to terminate an active decontamination process and de-energize the source(s) 20. The fob 51 or other remote control device can be limited to only an "ON" button 57 that activates a decontamination process, only an "OFF" button 55 that terminates a decontamination process, or a combination thereof.

Figure 5:
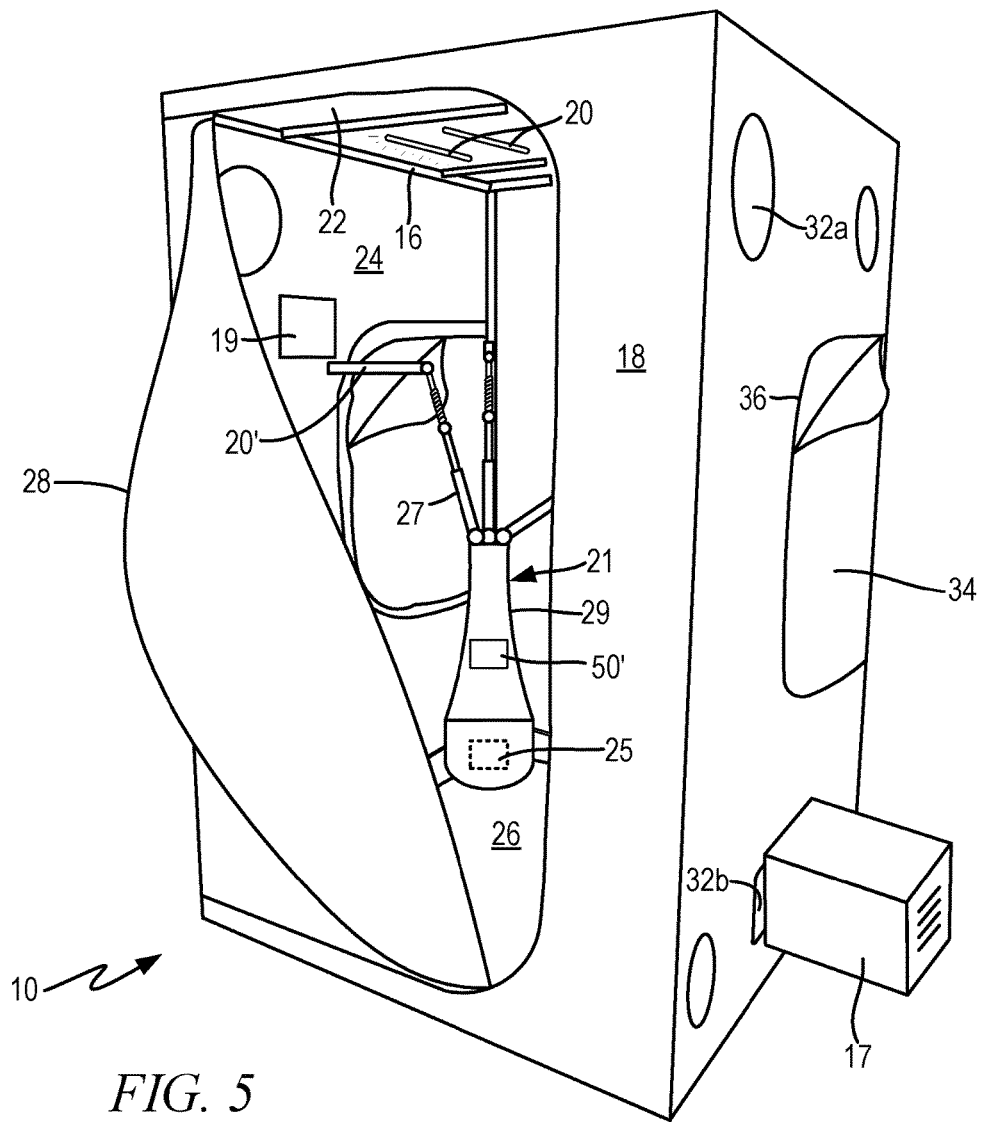
FIG. 5 is a perspective view of a decontamination booth in an open state, and housing a portable UVC decontamination apparatus as the UVC source.

Although the embodiments described above include the sources 20 of UVC light installed on the frame 16 as part of the decontamination booth 10, alternate embodiments can include a plurality of sources 20 provided to a portable UVC decontamination apparatus 21 (FIG. 5) that is placed inside the decontamination booth 10 along with the clinician 14. An example of such a portable UVC decontamination apparatus 21 is described in U.S. Pat. No. 9,095,633 to Dayton, which is incorporated in its entirety herein by reference. According to such embodiments, the decontamination booth 10 can be as described above, but separate from the sources 20 and optionally the controller 50', which can be provided to the portable UVC decontamination apparatus 21 itself as shown in FIG. 5. The portable UVC decontamination apparatus 21 of such embodiments can be independently arranged within the interior of the decontamination booth 10, as desired, and closed therein when the door flap 28 is closed. The one or a plurality of sources provided to such a portable UVC decontamination apparatus 21, each adjacent to an end of an adjustable arm such that the position of each source 20 can be adjusted relative to each other, and can be energized and optionally de-energized as described herein to achieve the desired level of decontamination, with the primary difference being that the portable UVC decontamination apparatus 21 can be arranged independently of the decontamination booth 10. Further, the position of each of a plurality of UVC light sources 20' provided to the portable UVC decontamination apparatus 21 can be independently adjusted relative to each other. Such adjustments can be achieved through manipulation of joints and/or other portions of adjustable arms 27 coupling the UVC light sources 20' to a base 29 of the portable UVC decontamination apparatus 21. The adjustable arms 27 allow for adjustment of the positions of the UVC light sources 20', even while the UVC light sources 20' are operational (e.g., emitting UVC light).

Figure 4:
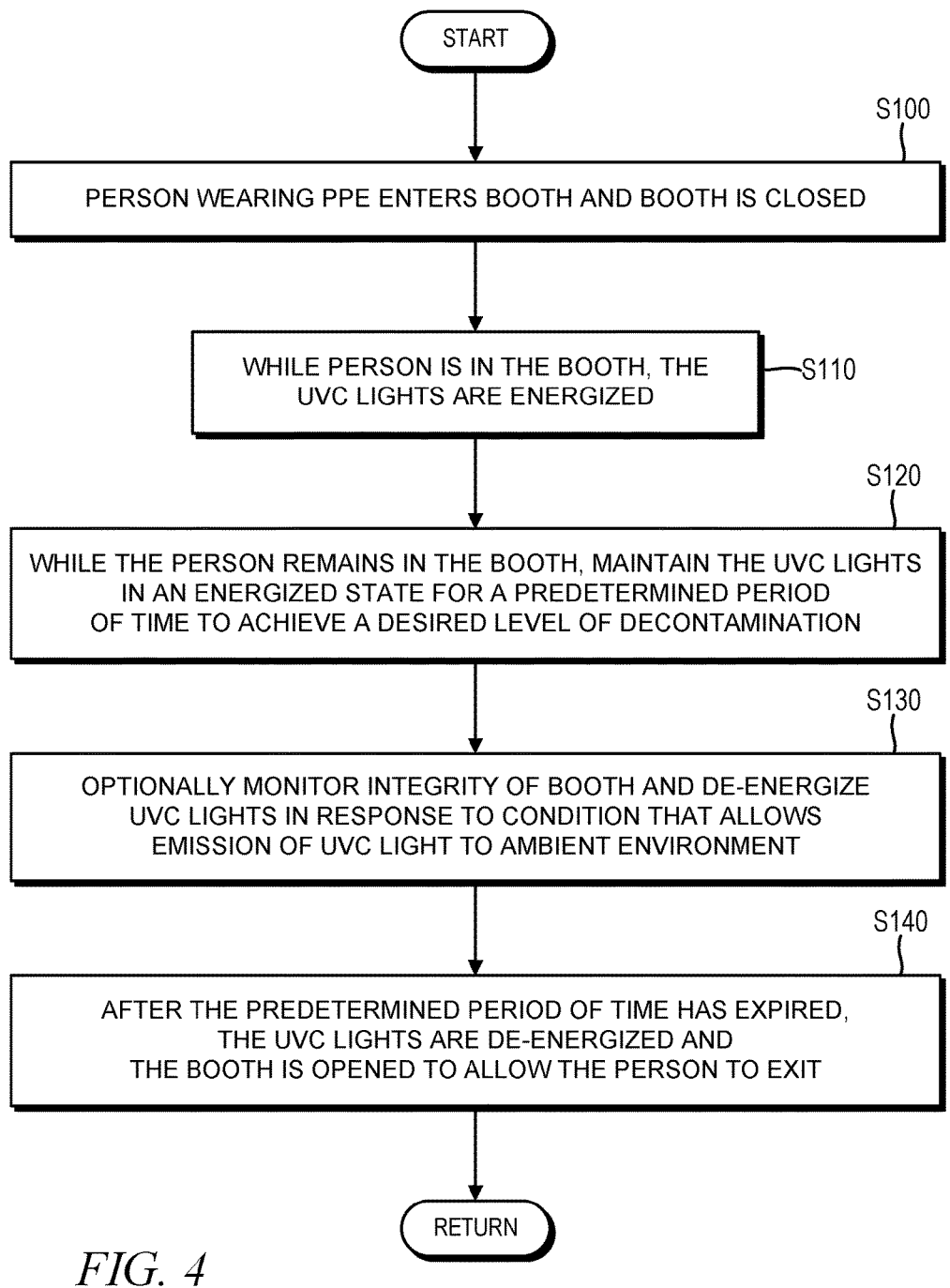
FIG. 4 is a flow diagram schematically depicting a method of decontaminating PPE while that PPE is being worn by a clinician following exposure to a pathogen.

FIG. 4 is a flow diagram schematically depicting a method of decontaminating the PPE 12 while it is being worn by the clinician 14 following possible exposure to a pathogen. As shown in FIG. 5, a placard 19 can optionally be secured to a wall 24 within the decontamination booth 10 and display to a person therein instructions on how to properly decontaminate PPE being worn by that person. The placard 19 can optionally guide the person in performing the following method. At step S100, the clinician 14 wearing the PPE 12 departs a location where a patient with an infectious disease is examined and enters the decontamination booth 10 through the open door flap 28 before the PPE 12 is removed. The clinician 14 or other person can then adjust the zipper to close the door flap 28 and close the interior window flap 38 provided to any open windows from within the decontamination booth 10. The clinician can also optionally stand atop of the platform 44, if present, to promote exposure of the clinician's footwear to reflected UVC light 46 during the decontamination process.

At step S110, an instruction can be input to the controller 50 to commence the decontamination process and energize the sources 20 while the clinician 14 wearing the PPE 12 is enclosed within the decontamination booth 10. This instruction can originate from any of the sources described herein, such as the start button 52 of the controller 50, a remotely-located fob, or any other suitable control device.

Once the decontamination process has begun, the timer 56 can monitor how long the sources 20 are active at step S120, maintaining operation of the sources 20 while the clinician 14 remains in the decontamination apparatus for a predetermined period of time that will achieve a desired level of decontamination. The clinician 14 can remain in the decontamination booth 10 while the sources 20 are energized without fearing harmful side effects of UVC exposure because the PPE 12 blocks virtually all of the UVC light, thereby preventing the UVC light from reaching the clinician's skin. Accordingly, the PPE 12 should offer full body protection, fully insulating the clinician 14 from the sources 12.

At step S130, one or more sensors can optionally monitor changes in visible light, motion within the decontamination booth 10, etc. to determine whether the light integrity of the decontamination booth 10 has been breached since the decontamination process was initiated. If so, the controller 50 can terminate the decontamination process and de-energize the sources 20. If not, however, the decontamination process is allowed to continue through expiration of the period established by the timer 56, at which time the sources 20 are de-energized and the clinician can exit the decontamination booth 10 at step S140. According to alternate embodiments, monitoring the integrity of the decontamination booth 10 to protect against the escape of UVC light to an ambient environment where others who are not protected by the PPE 12 could be exposed to escaping UVC light can include monitoring a status of the door flap 28 to detect when the door flap 28 has been opened. Such monitoring can be performed by sensing a status of a zipper assembly or other closure mechanism to determine when the door flap 28 has been opened or otherwise breached during a decontamination cycle. Similar monitoring can be performed to determine if a window (e.g., monitoring a zipper assembly or other closure device) has been breached in a manner that could potentially allow UVC light to escape the interior of the decontamination booth 10. Regardless of the type of monitoring performed, the sensing of any condition that could potentially allow UVC light to escape from the interior of the decontamination booth 10 into an unprotected ambient environment (e.g., where other people who are not wearing PPE 12 may be present) can result in premature (e.g., prior to successful completion of the decontamination cycle) termination of the decontamination cycle.

Although described above as decontaminating PPE 12 worn by a clinician 14 for the sake of brevity and clarity, the present disclosure is not so limited. Instead, the decontamination booth 10 and methods described herein can also be utilized to decontaminate inanimate objects such as wheelchairs, for example, as well.

Illustrative embodiments have been described, hereinabove. It will be apparent to those skilled in the art that the above devices and methods may incorporate changes and modifications without departing from the general scope of this invention. It is intended to include all such modifications and alterations within the scope of the present invention. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A decontamination apparatus comprising:
    a booth having a plurality of internally-reflective surfaces that define an interior space having dimensions suitable for receiving a standing person wearing personal protective equipment;
    a plurality of UVC light sources arranged to emit UVC light into the booth;
    a door that is selectively closeable to enclose the interior space and interfere with UVC light escaping the interior of the booth into an ambient environment of the booth; and
    a controller operable to selectively operate the UVC light sources while the person wearing the personal protective equipment is standing within the interior space, wherein the controller is accessible to, and operable by the person wearing the personal protective equipment from within the interior space to allow the person to control operation of the UVC light sources from within the interior space.

2. The decontamination apparatus of claim 1, wherein the controller comprises a timer operational to initiate deactivation of the UVC light sources after expiration of a predetermined period of time.

3. The decontamination apparatus of claim 2, wherein the predetermined period of time is selectable from a plurality of pre-programmed time periods stored by the controller.

4. The decontamination apparatus of claim 1 further comprising a vent provided to at least one side wall defining the interior space to allow an exchange of air between the interior space and the ambient environment.

5. The decontamination apparatus of claim 1, wherein the plurality of the UVC light sources are each coupled to an adjustable arm to render the UVC light sources adjustable relative to the interior space of the booth.

6. A decontamination apparatus comprising:
    a booth having a plurality of internally-reflective surfaces that define an interior space having dimensions suitable for receiving a standing person wearing personal protective equipment;
    a plurality of UVC light sources arranged to emit UVC light into the booth;
    a door that is selectively closeable to enclose the interior space and interfere with UVC light escaping the interior of the booth into an ambient environment of the booth; and
    a controller operable to selectively operate the UVC light sources while the person wearing the personal protective equipment is standing within the interior space,
    wherein the plurality of the UVC light sources are adjustable by the person from within the interior space while the UVC light sources are operational.

7. The decontamination apparatus of claim 6, wherein the plurality of the UVC light sources are each coupled to an adjustable arm to render the UVC light sources adjustable relative to the interior space of the booth.

8. The decontamination apparatus of claim 6, wherein the controller comprises a timer operational to initiate deactivation of the UVC light sources after expiration of a predetermined period of time.

9. The decontamination apparatus of claim 8, wherein the predetermined period of time is selectable from a plurality of pre-programmed time periods stored by the controller.

10. The decontamination apparatus of claim 6 further comprising a vent provided to at least one side wall defining the interior space to allow an exchange of air between the interior space and the ambient environment.

11. A decontamination apparatus further comprising:
    a booth having a plurality of internally-reflective surfaces that define an interior space having dimensions suitable for receiving an object;
    a plurality of UVC light sources arranged to emit UVC light into the booth;
    a door that is selectively closeable to enclose the interior space and interfere with UVC light escaping the interior of the booth into an ambient environment of the booth;
    a controller operable to selectively operate the UVC light sources while the object is within the interior space; and
    a platform comprising a surface that is substantially transparent to UVC light on which the object may be located to allow a bottom surface of the object to be exposed to the UVC light emitted by at least one of the UVC light sources.

12. The decontamination apparatus of claim 11 wherein the object includes at least one of personal protective equipment worn by a person, a wheelchair, or any other inanimate object.

13. A decontamination apparatus comprising:
a booth having a plurality of internally-reflective surfaces that define an interior space having dimensions suitable for receiving an object;
a plurality of UVC light sources arranged to emit UVC light into the booth;
a door that is selectively closeable to enclose the interior space and interfere with UVC light escaping the interior of the booth into an ambient environment of the booth;
a controller operable to selectively operate the UVC light sources while the object is within the interior space; and
a window provided to at least one side wall defining the interior space, the window being closed by a flexible material that is substantially transparent to visible light, but interferes with transmission of UVC light from the interior space to the ambient environment.

14. The decontamination apparatus of claim 13 wherein the object includes at least one of personal protective equipment worn by a person, a wheelchair, or any other inanimate object.

15. A decontamination apparatus comprising:
a booth having a rigid frame that supports a shell, the shell including a plurality of internally-reflective surfaces that define an interior space having dimensions suitable for receiving an object;
a plurality of UVC light sources arranged to emit UVC light into the interior space;
a door that is selectively closeable to enclose the interior space and interfere with UVC light escaping the interior of the booth into an ambient environment of the booth; and
a controller operable to selectively operate the UVC light sources while the object is within the interior space.

16. The decontamination apparatus of claim 15 wherein the rigid frame includes a plurality of interlocking segments.

17. The decontamination apparatus of claim 16 wherein the plurality of interlocking segments are configured to be assembled end to end by hand.

18. The decontamination apparatus of claim 16 wherein the plurality of interlocking segments are configured to be pulled apart and arranged to fit into a portable container to be carried by hand during relocation of the decontamination apparatus.

19. The decontamination apparatus of claim 15 wherein the shell includes at least one of a woven fabric or a cross-woven ballistic nylon.

20. The decontamination apparatus of claim 15 wherein the plurality of internally-reflective surfaces of the shell include an aluminized material configured to reflect the UVC light emitted by the plurality of UVC light sources.

* * * * *